United States Patent
Hirson et al.

(10) Patent No.: US 9,067,849 B2
(45) Date of Patent: Jun. 30, 2015

(54) SYSTEMS AND METHODS FOR PRODUCING FUEL FROM PARALLEL PROCESSED SYNGAS

(71) Applicant: Powerdyne, Inc., Newport Beach, CA (US)

(72) Inventors: Geoffrey Hirson, Newport Beach, CA (US); Gus F. Shouse, Newport Beach, CA (US)

(73) Assignee: POWERDYNE, INC., Newport Beach, CA (US)

( * ) Notice: Subject to any disclaimer, the term of this patent is extended or adjusted under 35 U.S.C. 154(b) by 0 days.

(21) Appl. No.: 14/206,591

(22) Filed: Mar. 12, 2014

(65) Prior Publication Data

US 2014/0275298 A1 Sep. 18, 2014

Related U.S. Application Data (60) Provisional application No. 61/778,021, filed on Mar. 12, 2013.

(51) Int. Cl.
*C07C 1/04* (2006.01)
*B01J 19/08* (2006.01)
(Continued)

(52) U.S. Cl.
CPC ............... *C07C 1/04* (2013.01); *B01J 19/088* (2013.01); *C01B 3/02* (2013.01); *B01J 8/02* (2013.01);
(Continued)

(58) Field of Classification Search
CPC ............. C07C 1/04; B01J 19/088; C01B 3/02
USPC ................... 518/702; 422/182.21; 252/373
See application file for complete search history.

(56) References Cited

U.S. PATENT DOCUMENTS

| 4,770,109 A | 9/1988 | Schlienger |
| 5,136,137 A | 8/1992 | Schlienger |

(Continued)

FOREIGN PATENT DOCUMENTS

| CA | 2379892 A1 | 2/2001 |
| CN | 1268550 A | 10/2000 |

(Continued)

OTHER PUBLICATIONS

Schuey et al., LLW Processing and Operational Experience Using a Plasma ARC Centrifugal Treatment (PACT) System, WM'06 Conference, Feb. 26-Mar. 2, 2006, Tucson, AZ.

(Continued)

*Primary Examiner* — Fereydoun G Sajjadi
*Assistant Examiner* — Medhanit Bahta
(74) *Attorney, Agent, or Firm* — Pepper Hamilton LLP (57) ABSTRACT

Systems and methods for fabricating syngas mixtures or fuels are disclosed. A system may include parallel processing chambers, each processing chamber configured to produce one component of a syngas mixture. Each chamber may include at least one plasma torch having a source of a working gas. In one embodiment, a first processing chamber may be optimized to produce hydrogen gas, and a second processing chamber may be optimized to produce carbon monoxide gas. The system may include a mixing component configured to mix the hydrogen gas and the carbon monoxide gas. The system may also include a reaction system to receive the hydrogen gas and the carbon monoxide gas and produce a fuel therefrom. The parallel processing chamber system may be used in methods for producing a syngas mixture or a fuel.

11 Claims, 3 Drawing Sheets

(51) Int. Cl.
*C01B 3/02* (2006.01)
*B01J 8/02* (2006.01)

(52) U.S. Cl.
CPC .......... *B01J 2208/00539* (2013.01); *B01J 2208/00628* (2013.01); *B01J 2219/0004* (2013.01); *B01J 2219/00058* (2013.01); *B01J 2219/00162* (2013.01); *B01J 2219/00186* (2013.01); *B01J 2219/0809* (2013.01); *B01J 2219/0875* (2013.01); *B01J 2219/0877* (2013.01)

(56) References Cited

U.S. PATENT DOCUMENTS

| | | |
|---|---|---|
| 5,138,959 A | 8/1992 | Kulkarni |
| 5,541,386 A | 7/1996 | Alvi et al. |
| 5,611,947 A | 3/1997 | Vavruska |
| 5,673,635 A | 10/1997 | Fowler |
| 5,725,616 A | 3/1998 | Lynum et al. |
| 6,187,226 B1 | 2/2001 | Detering et al. |
| 6,215,678 B1 | 4/2001 | Titus et al. |
| 6,289,851 B1 | 9/2001 | Rabovister et al. |
| 6,372,156 B1 | 4/2002 | Kong et al. |
| 6,505,567 B1 | 1/2003 | Anderson |
| 6,810,821 B2 | 11/2004 | Chan |
| 6,976,362 B2 | 12/2005 | Sheppard et al. |
| 7,070,634 B1 | 7/2006 | Wang |
| 7,279,655 B2 | 10/2007 | Blutke et al. |
| 7,384,619 B2 | 6/2008 | Bar-Gadda |
| 2002/0000085 A1 | 1/2002 | Hall et al. |
| 2003/0029796 A1 | 2/2003 | Maekawa |
| 2003/0065042 A1 | 4/2003 | Shaw |
| 2003/0209174 A1 | 11/2003 | Chan |
| 2006/0112639 A1 | 6/2006 | Nick et al. |
| 2006/0201157 A1 | 9/2006 | Villalobos |
| 2006/0233699 A1 | 10/2006 | Mills |
| 2007/0017228 A1 | 1/2007 | Surma |
| 2007/0186474 A1 | 8/2007 | Rabovitser et al. |
| 2007/0253874 A1 | 11/2007 | Foret |
| 2007/0266633 A1 | 11/2007 | Tsangaris et al. |
| 2007/0272131 A1 | 11/2007 | Carabin et al. |
| 2008/0041829 A1 | 2/2008 | Blutke et al. |
| 2008/0083701 A1 | 4/2008 | Shao et al. |
| 2008/0147241 A1 | 6/2008 | Tsangaris et al. |
| 2008/0184621 A1 | 8/2008 | Clark |
| 2008/0202028 A1 | 8/2008 | Tsangaris et al. |
| 2008/0209807 A1 | 9/2008 | Tsangaris et al. |
| 2008/0222956 A1 | 9/2008 | Tsangaris et al. |
| 2008/0223047 A1 | 9/2008 | Oliver |
| 2008/0277265 A1 | 11/2008 | Tsangaris et al. |
| 2008/0283153 A1 | 11/2008 | Zurecki et al. |
| 2008/0283411 A1 | 11/2008 | Eastman et al. |
| 2009/0038958 A1 | 2/2009 | Coyle et al. |
| 2009/0133407 A1 | 5/2009 | Sawyer |
| 2009/0307975 A1 | 12/2009 | Wolf |
| 2010/0065781 A1 | 3/2010 | Brothier |
| 2010/0229522 A1 | 9/2010 | Kingzett |
| 2010/0298449 A1 | 11/2010 | Rojey |
| 2011/0067376 A1 | 3/2011 | Tompkins et al. |
| 2011/0212012 A1 | 9/2011 | McAlister |
| 2011/0265698 A1 | 11/2011 | Hirson et al. |
| 2012/0000115 A1 | 1/2012 | Shastri |
| 2012/0070347 A1 | 3/2012 | Bacon et al. |
| 2012/0121468 A1 | 5/2012 | Tsangaris et al. |
| 2012/0291436 A1 | 11/2012 | Hirson et al. |
| 2013/0200624 A1 | 8/2013 | Hirson et al. |

FOREIGN PATENT DOCUMENTS

| | | |
|---|---|---|
| CN | 1810938 A | 8/2006 |
| EP | 1270508 A1 | 1/2003 |
| WO | WO 2005/005009 A2 | 1/2005 |
| WO | WO 2008/130260 A1 | 10/2008 |
| WO | WO 2009/156761 A2 | 12/2009 |
| WO | WO 2011/091327 A1 | 7/2011 |
| WO | WO 2011/140080 A2 | 11/2011 |
| WO | WO 2012/039751 A2 | 3/2012 |
| WO | WO 2012/064936 A1 | 5/2012 |
| WO | WO 2012/077198 A1 | 6/2012 |
| WO | WO 2012/158797 A1 | 11/2012 |
| WO | WO 2012/177666 A1 | 12/2012 |

OTHER PUBLICATIONS

Plasco Group, http://www.plascoenergygroup.com/our-solution/how-is-plasco-different/, retrieved from web Jul. 5, 2011.
International Search Report dated Jul. 28, 2014 for corresponding PCT Application No. PCT/US2014/024606.

SYSTEMS AND METHODS FOR PRODUCING FUEL FROM PARALLEL PROCESSED SYNGAS

CLAIM OF PRIORITY

This application claims benefit of and priority to U.S. Provisional Application Ser. No. 61/778,021 entitled "Systems and Methods for Producing Fuel From Parallel Processed Syngas" and filed Mar. 12, 2013, the disclosure of which is incorporated by reference herein in its entirety.

BACKGROUND

Fuel materials may take on a variety of forms from simple gases, such as hydrogen, to complex mixtures including aviation fuels. Due to their wide range of chemical compositions, chemical fuels may be generated through a variety of processes and may require facilities dedicated to synthesizing only a small number of possible fuel types. Such facilities may be optimized to generate only the fuels to which they are dedicated. Additionally, each facility may require a specific set of feed-stocks or precursor materials for fuel synthesis.

Typically, carbon-based fuels rely on thermal methods for their synthesis. Such methods may include pyrolysis, cracking, and endothermic synthesis steps. Such processes may generate excessive heat as a by-product of their synthetic methods. Further, such thermal chemistry-based synthetic methods may not be efficient even for an optimized facility.

Syngas presents an alternative feedstock from which a variety of fuels may be produced. Syngas is composed primarily of a mixture of hydrogen and carbon monoxide gases. These two components may be used under a variety of synthetic conditions to create several different types of fuel material. It is, therefore, desirable to have a production facility capable of synthesizing syngas having specified proportions of hydrogen and carbon monoxide and which can then be used to produce a wide variety of fuels. It may further be desirable for such a production facility to optimize the production of such fuels and syngas through the reduction or prevention of soot formation during the formation of hydrogen gas and carbon monoxide gas.

SUMMARY

The invention described in this document is not limited to the particular systems, methodologies or protocols described, as these may vary. The terminology used herein is for the purpose of describing particular embodiments only, and is not intended to limit the scope of the present disclosure.

It must be noted that as used herein, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, a system may be composed of a first primary processing chamber in operable communication with a source of water through a water inlet. The first primary processing chamber may further include at least one first plasma torch, a first source of a first ionizing working gas for introduction into the at least one first plasma torch, a first oxygen gas outlet, a hydrogen gas outlet, and a water vapor outlet. The system may further include a second primary processing chamber in operable communication with a source of carbon dioxide through a carbon dioxide inlet and oxygen through the first oxygen outlet. The second primary processing chamber may further include at least one second plasma torch, a second source of a second ionizing working gas for introduction into the at least one second plasma torch, a second oxygen gas outlet, a carbon monoxide gas outlet, and a carbon dioxide gas outlet. The system may further include a mixing component in fluid communication with the hydrogen gas outlet and the carbon dioxide gas outlet.

In an embodiment, a method of synthesizing syngas may include providing a system for synthesizing syngas in which the system may include a first primary processing chamber having at least one first plasma torch, a first source of a first ionizing working gas for introduction into the at least one first plasma torch, a first oxygen outlet, a hydrogen gas outlet, and a water vapor outlet, a second primary processing chamber in operable communication with a source of oxygen through the first oxygen outlet, having at least one second plasma torch, a second source of a second ionizing working gas for introduction into the at least one second plasma torch, a second oxygen outlet, a carbon monoxide gas outlet, and a carbon dioxide gas outlet, and a mixing component in fluid communication with the hydrogen gas outlet and the carbon dioxide gas outlet, introducing water into the first primary processing chamber from a water source, causing the first processing chamber to emit hydrogen gas from the hydrogen gas outlet, introducing carbon dioxide gas into the second primary processing chamber from a carbon dioxide source, causing the second processing chamber to emit carbon monoxide gas from the carbon monoxide gas outlet, and combining the hydrogen gas and the carbon monoxide gas by the mixing component to produce a syngas.

In an embodiment, a method of synthesizing a fuel may include providing a system for synthesizing syngas in which the system may include a first primary processing chamber having at least one first plasma torch, a first source of a first ionizing working gas for introduction into the at least one first plasma torch, a first oxygen outlet, a hydrogen gas outlet, and a water vapor outlet, a second primary processing chamber in operable communication with a source of oxygen through the first oxygen outlet, having at least one second plasma torch, a second source of a second ionizing working gas for introduction into the at least one second plasma torch, a second oxygen outlet, a carbon monoxide gas outlet, and a carbon dioxide gas outlet, and a mixing component in fluid communication with the hydrogen gas outlet and the carbon dioxide gas outlet, introducing water into the first primary processing chamber from a water source, causing the first processing chamber to emit hydrogen gas from the hydrogen gas outlet, introducing carbon dioxide gas into the second primary processing chamber from a carbon dioxide source, causing the second processing chamber to emit carbon monoxide gas from the carbon monoxide gas outlet, and reacting the hydrogen gas and the carbon monoxide gas in a reaction system thereby producing a fuel.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 1:
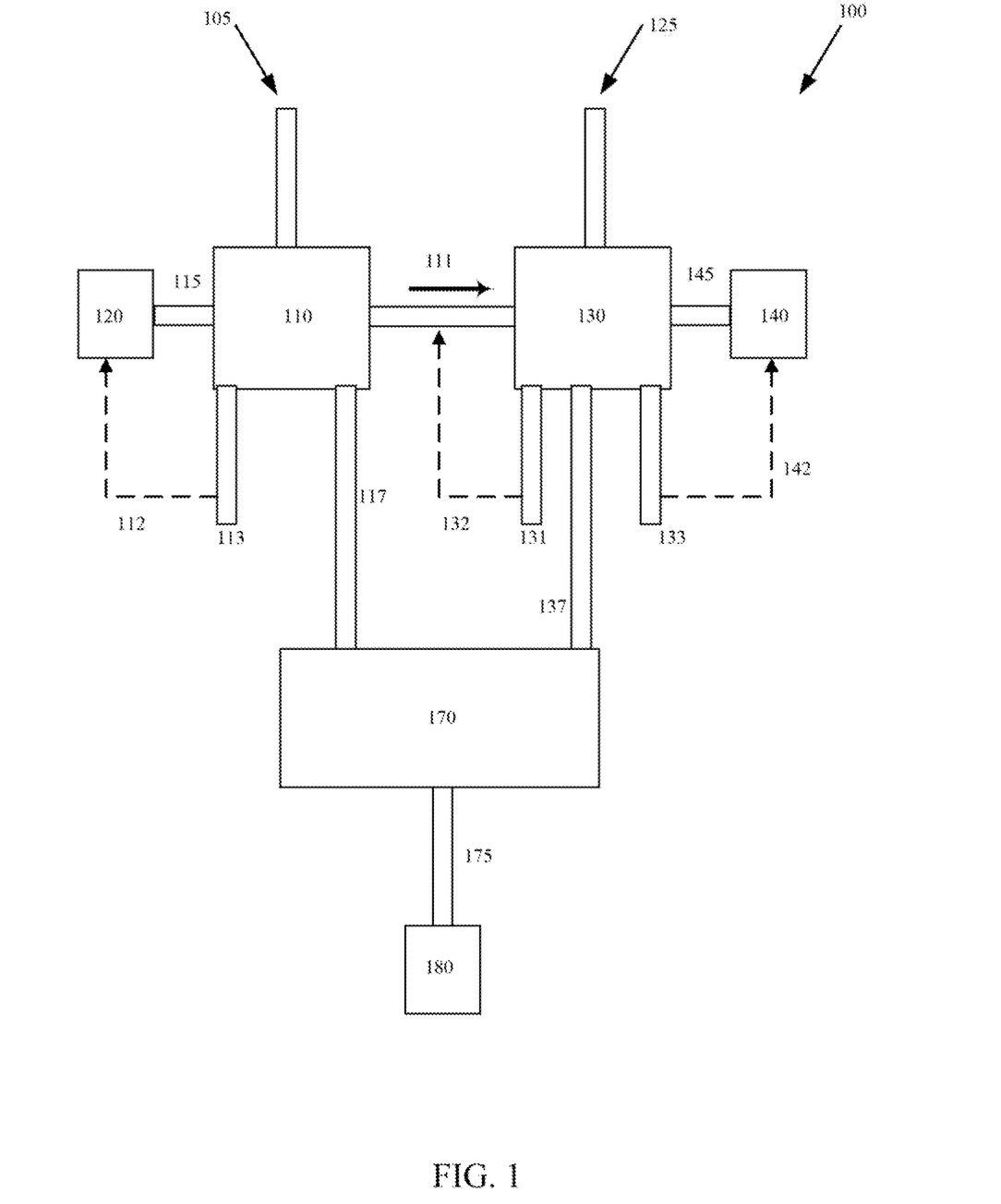
FIG. 1 illustrates an embodiment of a system for synthesizing a fuel from components of syngas in accordance with the present disclosure.

As shown in FIG. 1, the system 100 may include parallel paths for gas production. Each path may be optimized for the synthesis of a primary component of a syngas. One arm of the system includes a first primary processing chamber ("PPC1") 110 that includes a housing constructed to withstand the internal temperatures generated by one or more plasma arc torches 105 as described below. Depending on the system design requirements, the construction of the PPC1 housing may further include an active cooling system and/or an insulating lining PPC1 110 may include a water inlet 115 for water supplied by a water source 120, and separate outlets for oxygen 111, water vapor 113, and hydrogen gas 117, but may otherwise be sealed so that no gases may escape. The construction of the PPC1 housing may be sufficient to maintain a vacuum pressure, such as a pressure between 0 pounds per square inch of vacuum (PSIV) and about 14.7 PSIV, without rupturing.

PPC1 110 may additionally contain one or more plasma arc torches 105 that may be used to heat the contents of PPC1. It may be appreciated that the one or more plasma arc torches 105 may be a source of both heat and an ionized working gas that may convert the water into hydrogen and oxygen. The one or more plasma arc torches 105 may be capable of elevating the temperature in PPC1 110 to a temperature of about 350° F. to about 36,000° F. (about 180° C. to about 20,000° C.). As non-limiting examples, the plasma arc torches may be activated to heat the gas to a desired temperature, of about 350° F., about 1000° F., about 2000° F., about 2200° F., about 2400° F., about 2500° F., about 2850° F., about 3500° F., about 5000° F., about 10000° F., about 20000° F., about 30000° F., about 36000° F., or a range of temperatures between any two of these values (including endpoints). Various types of plasma arc torches may be used. A non-transferred plasma arc torch may house both the anode and the cathode, the cathode being downstream of the anode. In operation, the arc may be drawn within a plasma arc torch, and the plasma may extend beyond the end of the plasma arc torch as a result of high gas flow through the plasma arc torch. Optionally, a non-transferred arc plasma arc torch may be fitted with a gas backflow collar so that gas is not vented to the atmosphere.

In one alternative embodiment, the water source 120 may provide liquid water to PPC1 110 as a fine mist or spray emanating from the water inlet 115. Alternatively, pre-heated water may be used, and the water inlet 115 may provide water as steam to the interior of PPC1 110. In some embodiments, the water inlet 115 may further include a nozzle that is positioned at an angle with respect to the inner walls of PPC1 110 so that it introduces the water into the chamber at a direction to create turbulence and facilitate movement of the water into the one or more plasma arc torches' arcs.

Any of a group of valves and/or pumps may be used to cause the water to enter PPC1 110. It may be understood that such valves and/or pumps may be under either manual control or automated process control by a system process controller. In this manner, the amount of water entering PPC1 110 may be controlled depending on the temperature or pressure of PPC1. In addition, the amount of water delivered to PPC1 110 may be varied by the valve and/or pump components to adjust the amount of hydrogen produced by PPC1 and transferred through the hydrogen gas outlet 117 for use downstream (see below). Hydrogen gas may be separated out from the reaction products of PPC1 110 based on temperature or molecular weight. In one non-limiting example, hydrogen gas may be separate from other components using a membrane. In another non-limiting example, hydrogen gas may be separated from other components by means of a molecular sieve. Excess water, as steam, may be vented from PPC1 110 through a water vapor outlet 113. It may be appreciated that this water vapor may be vented to the atmosphere or may be recycled back 112 to the water source 120 for reuse. It may be appreciated that the amount of water recycled back 112 to the water source 120 may be under the control of one or more sensors and valves. Such sensors may provide information to a system process controller. Valves to direct the amount of water recycled back 112 to the water source 120 may be under manual control or automated process control via a system process controller. Temperature, pressure and gas composition sensors associated with PPC1 110 may provide data to the system process controller to determine how much excess water may be returned to PPC1 for re-use.

Oxygen gas produced by PPC1 110 may be diverted through an oxygen outlet 111 to a second processing chamber, PPC2 130. Although not illustrated in FIG. 1, it may be appreciated that the oxygen outlet 111 may include any number and type of valves and/or pumps designed to assure that the oxygen produced by PPC1 110 is routed in a unidirectional manner into PPC2 130. Such valves and/or pumps may be manually operated or may be under control by the system process controller. The valves and/or pumps not only may assure the directional flow of the oxygen, but also may function to meter the amount of oxygen introduced into PPC2 130. Such metering may be useful to optimize the reaction products produced by PPC2 130. In one non-limiting example, the amount of oxygen gas entering PPC2 130 may be controlled so that a ratio of carbon monoxide gas and hydrogen gas to carbon dioxide gas and water vapor (that is, $[CO+H_2]/[CO_2+H_2O]$) is maintained in a range of about 0.2 to about 0.4 to reduce or prevent the formation of soot in PPC2 130. Sensors within the oxygen outlet 111 may also provide process information such as the temperature of the oxygen as well as its purity. Data from the oxygen outlet 111 sensors may be provided to the system process controller to adjust any of the process parameters associated with PPC2 130 or its associated components. Oxygen gas may be separated out from the reaction products of PPC1 110 based on temperature or molecular weight. In one non-limiting example, oxygen gas may be separated from other components using a membrane. In another non-limiting example, oxygen may be separated from other components by means of a molecular sieve.

In addition to the oxygen outlet 111 from PPC1 110, PPC2 130 may also include one or more second plasma arc torches 125 which may be controlled by the system process controller independently of the control of the one or more plasma arc torches 105 associated with PPC1 110. It may be appreciated that the one or more plasma arc torches 125 may be a source of both heat and an ionized working gas that may convert the carbon dioxide and oxygen into carbon monoxide. The one or more second plasma arc torches 125 may be controlled to have temperatures suitable for the operation of PPC2 130. While PPC1 110 may be configured specifically to react water to form hydrogen, PPC2 130 may be primarily configured to produce additional or alternative output gases. In one non-limiting embodiment, PPC2 130 may be specifically configured to use carbon dioxide. Carbon dioxide may be supplied from a carbon dioxide source 140 and may enter PPC2 130 through a carbon dioxide inlet 145. In some embodiments, the carbon dioxide inlet 145 may further include a nozzle that is positioned at an angle with respect to the inner walls of PPC2 130 so that it introduces the carbon dioxide into the chamber at a direction to create turbulence and facilitate movement of the carbon dioxide into the one or more second plasma arc torches' arc.

Any of a group of valves and/or pumps may be used to cause the carbon dioxide to enter PPC2 130. It may be understood that such valves and/or pumps may be under either manual control or automated process control by a system process controller. In this manner, the amount of carbon dioxide entering PPC2 130 may be controlled depending on the temperature or pressure of PPC2. In addition, the amount of carbon dioxide delivered to PPC2 130 may be varied by the valve and/or pump components to adjust the amount of carbon monoxide produced by PPC2 and transferred through the carbon monoxide gas outlet 137 for use downstream (see below). Carbon monoxide gas may be separated out from the reaction products of PPC2 130 based on temperature or molecular weight. In one non-limiting example, carbon monoxide gas may be separated from other components using a membrane. In another non-limiting example, carbon monoxide may be separated from other components by means of a molecular sieve.

Excess carbon dioxide, may be vented from PPC2 130 through a carbon dioxide outlet 133. It may be appreciated that this carbon dioxide may be vented to the atmosphere, or may be recycled back 142 to the carbon dioxide source 140 for reuse. It may be appreciated that the amount of carbon dioxide recycled back 142 to the carbon dioxide source 140 may be under the control of one or more sensors and valves. Such sensors may provide information to a system process controller. Valves to direct the amount of carbon dioxide recycled back 142 to the carbon dioxide source 140 may be under manual control or automated process control via a system process controller. Similarly, excess oxygen may be vented to the atmosphere through oxygen outlet 131. Alternatively, the excess oxygen may be recycled back 132 into PPC2 130 through the oxygen inlet line 111. It may be appreciated that the amount of oxygen recycled back 122 to the oxygen inlet line 111 may be under the control of one or more sensors and valves. Such sensors may provide information to a system process controller. Valves to direct the amount of oxygen recycled back 122 to the oxygen inlet line 111 may be under manual control or automated process control via a system process controller. Any number of control valves and/or pumps may be used to control the amount of either excess carbon dioxide or oxygen recycled or vented to the atmosphere. Temperature, pressure and gas composition sensors associated with PPC2 130 may provide data to the system process controller to determine how much of each of these gases may be returned to PPC2 for re-use.

It may be appreciated that the hydrogen gas produced from PPC1 110 and the carbon monoxide produced from PPC2 130 together comprise the primary components of syngas. It may be appreciated that the production of the two syngas components in parallel may provide significant control over the character of the syngas thus produced. As a result, fuel material produced from the syngas—for example, through a Fischer-Tropsch reaction system 170—may be tailored according to need based at least in part on the composition of the syngas. In one non-limiting embodiment, the hydrogen gas outlet 117 and the carbon monoxide gas outlet 137 may be joined at a confluence (not illustrated) in which the two gases are mixed prior to their introduction to the Fischer-Tropsch reaction system 170. The confluence may include any number of sensors and valves to allow dynamic selection of the two gases. Such sensors may include gas composition sensors, heat sensors, and pressure sensors. The data output from such sensors may be transmitted to the system process controller, which may use the data from the confluence sensors to adjust any of a number of upstream components, including plasma arc torch temperatures for either PPC, water supplied to PPC1 110, and/or carbon dioxide supplied to PPC2 130.

The Fischer-Tropsch reaction system 170 may contain a Fischer-Tropsch type (F-T) catalyst. The F-T catalyst may be composed of one or more of cobalt, iron, ruthenium, nickel, copper, an alkali metal oxide, silica, alumina, and a zeolite. The syngas, delivered either through a separate hydrogen gas outlet 117 and a carbon monoxide gas outlet 137 or through an outlet of a confluence, may be introduced into the Fischer-Tropsch reaction system 170. The Fischer-Tropsch reaction system 170 may include, without limitation, the F-T catalyst as well as mechanical and electrical components required to perform the F-T reaction. Such mechanical and electrical components may include process-controlled valves, pumps, pressure and temperature sensors, and/or temperature control systems. The resulting fuel or fuels produced in the Fischer-Tropsch reaction system 170 may be captured in one or more containment vessels 180 through one or more reaction system outlets 175. In some non-limiting examples, the fuel may be composed of diesel fuel, JP-8 fuel, jet fuel, naphtha, and synthetic paraffinic kerosene. Other petrochemicals and fuels may also be manufactured in this manner.

It may be appreciated that typical temperatures for a Fischer-Tropsch reaction system 170 may be within a range of about 150 degrees C. to about 300 degrees C., temperatures that may be significantly below the temperatures of the hydrogen and carbon monoxide gases generated by PPC1 110 and PPC2 130, respectively. Therefore, a cooling step may be required for the syngas components prior to their introduction into the Fischer-Tropsch reaction system 170. Excess heat removed from the hydrogen gas and carbon monoxide gas may additionally be used within the system. In one non-limiting example, excess heat may be used to preheat water from the water source 120, the carbon dioxide from the carbon dioxide source 140, or the oxygen outlet 111 from PPC1 110 to PPC2 130. Alternatively, the excess heat may be used to heat the working gases used by the plasma arc torches 105 and 125. In an alternative example, the excess heat may be used to produce power by generating steam through one or more heat recovery steam generators (HRSG's).

Figure 2:
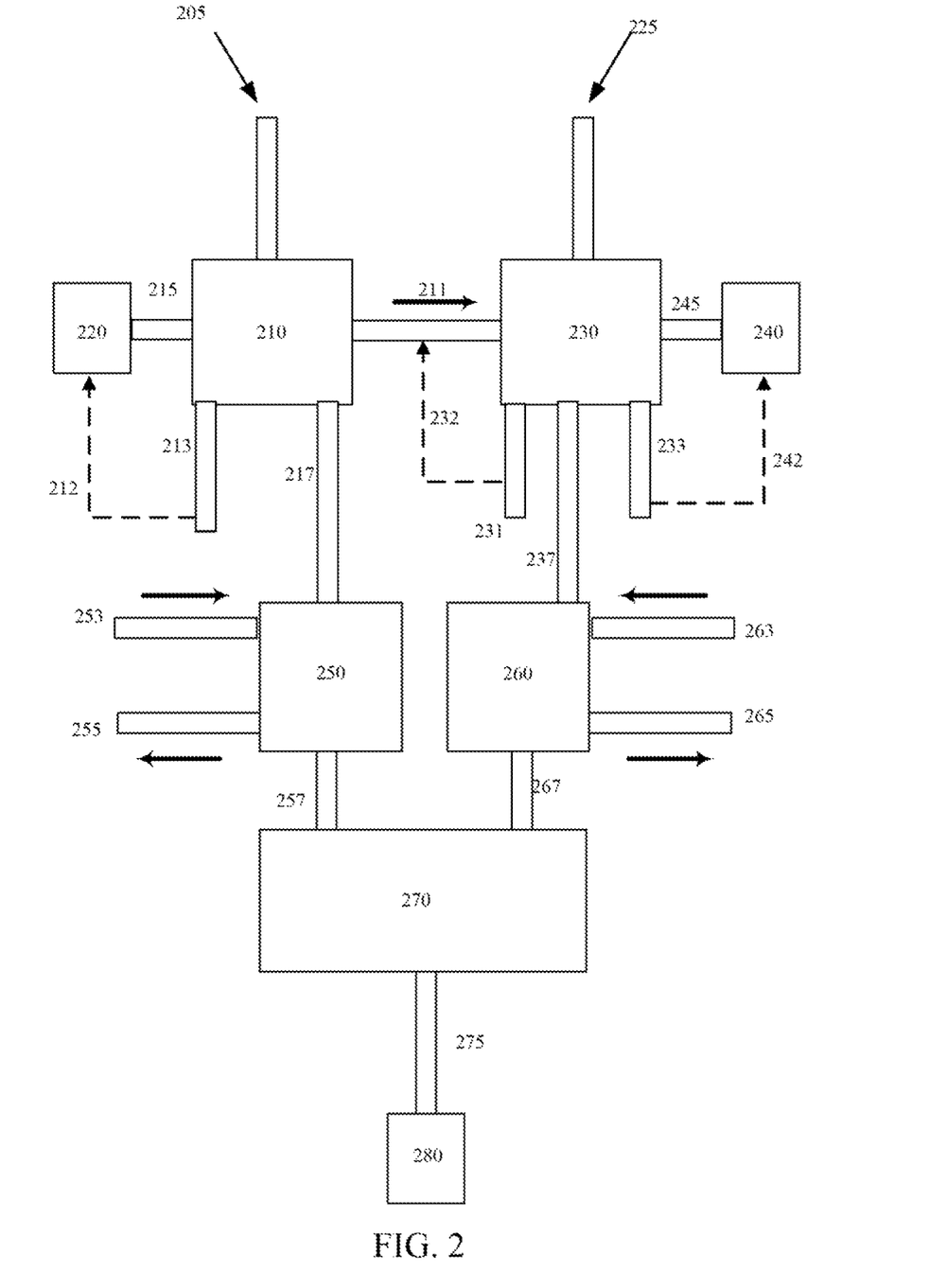
FIG. 2 illustrates an embodiment of a system for synthesizing both fuel and power from components of syngas in accordance with the present disclosure.

FIG. 2 illustrates a system in which such excess heat may be used to provide power through one or more HRSG's. Many of the components in FIG. 2 are similar to those in FIG. 1 and may function in similar manners. The system illustrated in FIG. 2 may include parallel paths for gas production, each path optimized for the synthesis of a primary component of syngas. One arm of the system includes a first primary processing chamber ("PPC1") 210 that includes a housing constructed to withstand the internal temperatures generated by one or more plasma arc torches 205 as described below. Depending on the system design requirements, the construction of PPC1 housing may further include an active cooling system and/or an insulating lining. PPC1 210 may include a water inlet 215 for water supplied by a water source 220, and separate outlets for oxygen 211, water vapor 213, and hydrogen gas 217, but may otherwise be sealed so that no gases may escape. The construction of PPC1 housing may be sufficient to maintain a vacuum pressure, such as a pressure between 0 PSIV to about 14.7 PSIV, without rupturing.

PPC1 210 may additionally contain one or more plasma arc torches 205 that may be used to heat the contents of PPC1. It may be appreciated that the one or more plasma arc torches 205 may be a source of both heat and an ionized working gas that may convert the water into hydrogen and oxygen. The one or more plasma arc torches 205 may be capable of elevating the temperature in PPC1 210 to a temperature of about 350° F. to about 36,000° F. (about 180° C. to about 20,000° C.). As non-limiting examples, the plasma arc torches may be activated to heat the gas to a desired temperature, of about 350° F., about 1000° F., about 2000° F., about 2200° F., about 2400° F., about 2500° F., about 2850° F., about 3500° F., about 5000° F., about 10000° F., about 20000° F., about 30000° F., about 36000° F., or a range of temperatures between any two of these values (including endpoints). Various types of plasma arc torches may be used. A non-transferred-arc plasma arc torch may house both the anode and the cathode, the cathode being downstream of the anode. In operation, the arc may be drawn within a plasma arc torch, and the plasma may extend beyond the end of the plasma arc torch as a result of high gas flow through the plasma arc torch. In one non-limiting embodiment, a non-transferred plasma arc torch may be fitted with a gas backflow collar so that gas is not vented to the atmosphere.

In one alternative embodiment, the water source 220 may provide liquid water to PPC1 210 as a fine mist or spray emanating from the water inlet 215. Alternatively, pre-heated water may be used, and the water inlet 215 may provide water as steam to the interior of PPC1 210. In some embodiments, the water inlet 215 may further include a nozzle that is positioned at an angle with respect to the inner walls of PPC1 210 so that it introduces the water into the chamber at a direction to create turbulence and facilitate movement of the water into the plasma arc torch's arc.

Any of a group of valves and/or pumps may be used to cause the water to enter PPC1 210. It may be understood that such valves and/or pumps may be under either manual control or automated process control by a system process controller. In this manner, the amount of water entering PPC1 210 may be controlled depending on the temperature or pressure of PPC1. In addition, the amount of water delivered to PPC1 210 may be varied by the valve and/or pump components to adjust the amount of hydrogen produced by PPC1 and transferred through the hydrogen gas outlet 217 for use downstream (see below). Excess water, as steam, may be vented from PPC1 210 through a water vapor outlet 213. It may be appreciated that this water vapor may be vented to the atmosphere or may be recycled back 212 to the water source 220 for reuse. Temperature, pressure and gas composition sensors associated with PPC1 210 may provide data to the system process controller to determine how much excess water may be returned to PPC1 for re-use.

Oxygen gas produced by PPC1 210 may be diverted through an oxygen outlet 211 to a second processing chamber, PPC2 230. Although not illustrated in FIG. 2, it may be appreciated that oxygen outlet 211 may include any number and type of valves and/or pumps designed to assure that the oxygen produced by PPC1 210 is routed in a unidirectional manner into PPC2 230. Such valves and/or pumps may be manually operated or may be controlled by the system process controller. The valves and/or pumps not only may assure the directional flow of the oxygen, but also may function to meter the amount of oxygen introduced into PPC2 230. Such metering may be useful to optimize the reaction products produced by PPC2 230. Sensors within the oxygen outlet 211 may also provide process information, such as the temperature of the oxygen as well as its purity. Data from the oxygen outlet 211 sensors may be provided to the system process controller to adjust any of the process parameters associated with PPC2 230 or its associated components.

In addition to the oxygen outlet 211 from PPC1 210, PPC2 230 may also include one or more second plasma arc torches 225 which may be controlled by the system process controller independently of the control of the one or more plasma arc torches 205 associated with PPC1 210. It may be appreciated that the one or more second plasma arc torches 225 may be a source of both heat and an ionized working gas that may convert the carbon dioxide and oxygen into carbon monoxide. The one or more second plasma arc torches 225 may be controlled to have temperatures suitable for the operation of PPC2 230. While PPC1 210 may be configured specifically to react water to form hydrogen, PPC2 230 may be primarily configured to produce additional or alternative output gases. In one non-limiting embodiment, PPC2 230 may be specifically configured to use carbon dioxide. Carbon dioxide may be supplied from a carbon dioxide source 240 and may enter PPC2 230 through a carbon dioxide inlet 245. In some embodiments, the carbon dioxide inlet 245 may further include a nozzle that is positioned at an angle with respect to the inner walls of PPC2 230 so that it introduces the carbon dioxide into the chamber at a direction to create turbulence and facilitate movement of the carbon dioxide into the plasma arc torch's arc.

Any of a group of valves and/or pumps may be used to cause the carbon dioxide to enter PPC2 230. It may be understood that such valves and/or pumps may be under either manual control or automated process control by a system process controller. In this manner, the amount of carbon dioxide entering PPC2 230 may be controlled depending on the temperature or pressure of PPC2. In addition, the amount of carbon dioxide delivered to PPC2 230 may be varied by the valve and/or pump components to adjust the amount of carbon monoxide produced by PPC2 and transferred through the carbon monoxide gas outlet 237 for use downstream (see below).

Excess carbon dioxide, may be vented from PPC2 230 through a carbon dioxide outlet 233. It may be appreciated that this carbon dioxide may be vented to the atmosphere, or may be recycled back 242 to the carbon dioxide source 240 for reuse. Similarly, excess oxygen may be vented to the atmosphere through oxygen outlet 231. Alternatively, the excess oxygen may be recycled back 232 into PPC2 230 through the oxygen inlet line 211. Any number of control valves and/or pumps may be used to control the amount of either excess carbon dioxide or oxygen recycled or vented to the atmosphere. Temperature, pressure and gas composition sensors associated with PPC2 230 may provide data to the system process controller to determine how much of each of these gases may be returned to PPC2 for re-use.

It may be appreciated that the hydrogen gas produced from PPC1 210 and carbon monoxide produced from PPC2 230 together comprise the primary components of syngas. It may be appreciated that the production of the two syngas components in parallel may provide significant control over the character of the syngas thus produced. As a result, fuel material produced from the syngas—for example, through a Fischer-Tropsch reaction system 270—may be tailored according to need based at least in part on the composition of the syngas.

As disclosed above, excess heat from the hydrogen gas in the hydrogen gas outlet 217 and the carbon monoxide gas in the carbon monoxide gas outlet 237 may be used to preheat gas components entering either PPC1 210 or PPC2 230. Alternatively, such excess heat may be converted to useful power through one or more heat recovery steam generators (HRSG's). As illustrated in one non-limiting embodiment in FIG. 2, the hydrogen gas outlet 217 may serve as an input to a first HRSG (HRSG1) 250, and the carbon monoxide gas outlet 237 may serve as an input to a second HRSG (HRSG2) 260. HRSG1 may have a first heat exchange inlet 253 and first heat exchange outlet 255 thus permitting the excess heat from the hydrogen gas to heat a working fluid (such as water) for use in a power generation system, such as a gas turbine. It may be apparent to one skilled in the art how such a recirculating heated fluid system may be used in a gas turbine to generate electricity. In a similar manner, HRSG2 may have a second heat exchange inlet 263 and second heat exchange outlet 265 thus permitting the excess heat from the carbon monoxide gas to heat a working fluid (such as water) for use in a power generation system, such as a gas turbine.

Although FIG. 2 illustrates an embodiment in which the hydrogen gas outlet 217 may couple with HRSG1 250 and the carbon monoxide gas outlet 237 may couple with HRSG2 260, it may be appreciated that alternative configurations are contemplated by this disclosure. In one non-limiting example, HRSG1 250 and HRSG2 260 may have heat exchange inlets (253 and 263, respectively) and heat exchange outlets (255 and 265, respectively) connected to separate gas turbine systems. In another non-limiting example, HRSG1 250 and HRSG2 260 may have heat exchange inlets (253 and 263, respectively) and heat exchange outlets (255 and 265, respectively) connected to the same gas turbine system. In one non-limiting example, a single HRSG may contain two separate lines, one for the hydrogen gas and one for the carbon monoxide gas, the single HRSG configured to exchange heat from both gases with one or more gas turbine systems. In still another non-limiting example, a single HRSG may be provided to serve as a confluence for the hydrogen gas and carbon monoxide gas, so that the two gases mix together within the HRSG as they exchange their excess heat with a working fluid to power one or more gas turbine systems. It may be appreciated that a HRSG acting as a confluence for the two gases may also include a variety of valves and sensors in communication with the system process controller, thereby permitting the system process controller to change the mixture of gases within the HRSG via actuation of appropriate valves in order to optimize a particular fuel production.

The non-limiting example of a system illustrated in FIG. 2 depicts separate HRSG's, one associated with hydrogen production (HRSG1, 250) and one associated with carbon monoxide production (HRSG2, 260). HRSG1 250 may have a first HRSG outlet line 257 that may direct the cooled hydrogen gas to the Fischer-Tropsch reaction system 270. Similarly, HRSG2 260 may have a second HRSG outlet line 267 that may direct the cooled carbon monoxide gas to the Fischer-Tropsch reaction system 270. In one non-limiting embodiment, first HRSG outlet line 257 and second HRSG outlet line 267 may be joined at a confluence (not illustrated) in which the two gases may be mixed prior to their introduction into the Fischer-Tropsch reaction system 270. The confluence may include any number of sensors and valves to allow dynamic selection of the two gases, thereby permitting the system process controller to change the mixture of gases exiting the confluence via actuation of appropriate valves. Sensors within the confluence may include gas composition sensors, heat sensors, and pressure sensors. The data output from these sensors may be transmitted to the system process controller, which may use the data from the confluence sensors to adjust any of a number of upstream components, including plasma arc torch temperatures for either PPC, water supplied to PPC1 210, and/or carbon dioxide supplied to PPC2 230.

The Fischer-Tropsch reaction system 270 may contain an F-T catalyst. The F-T catalyst may be composed of one or more of cobalt, iron, ruthenium, nickel, copper, an alkali metal oxide, silica, alumina, and a zeolite. The syngas, delivered either through separate first HRSG outlet line 257 and second HRSG outlet line 267 or through an outlet of a confluence, may be introduced into the Fischer-Tropsch reaction system 270. The Fischer-Tropsch reaction system 270 may include, without limitation, the F-T catalyst as well as mechanical and electrical components required to perform the F-T reaction. Such mechanical and electrical components may include process-controlled valves, pumps, pressure and temperature sensors, and/or temperature control systems. The resulting fuel or fuels produced in the Fischer-Tropsch reaction system 270 may be captured in one or more containment vessels 280 through one or more reaction system outlets 275. In some non-limiting examples, the fuel may be composed of diesel fuel, JP-8 fuel, jet fuel, naphtha, and synthetic paraffinic kerosene. Other petrochemicals and fuels may also be manufactured in this manner.

Figure 3:
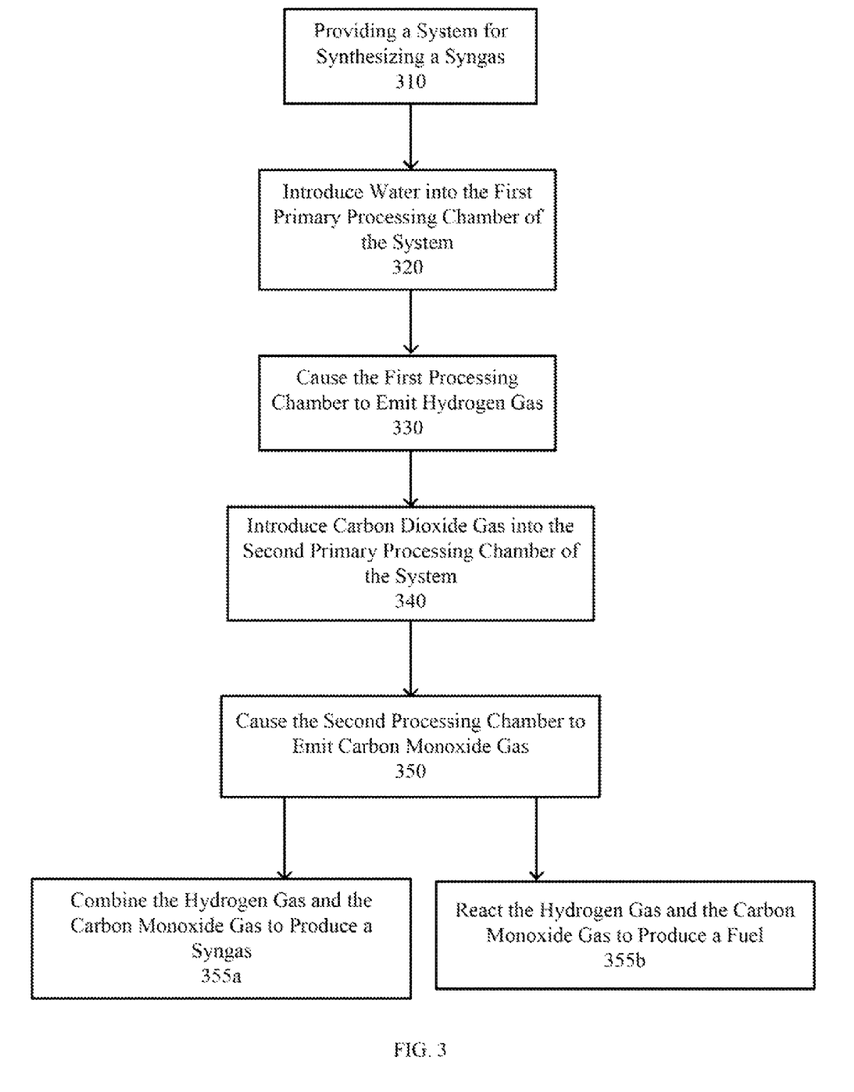
FIG. 3 is a flow chart of a method of producing a syngas or a fuel from a syngas in accordance with the present disclosure.

FIG. 3 is a flow chart of embodiments of methods of synthesizing a syngas and/or a fuel from a parallel processing syngas system. The method includes providing 310 a parallel processing syngas system as disclosed above and in FIGS. 1 and 2. Such a parallel processing syngas system may include two processing chambers, a first chamber configured to produce hydrogen gas from water through the use of at least one first plasma torch, and a second chamber configured to produce carbon monoxide gas from carbon dioxide and oxygen through the use of at least one second plasma torch. Water may be introduced 320 into the first processing chamber and at least a portion of the water may be converted to hydrogen gas through the action of the at least one first plasma torch. The first processing chamber may emit 330 the hydrogen gas produced therein. Carbon dioxide gas may be introduced 340 into the second chamber with the addition of excess oxygen, and at least a portion of the carbon dioxide gas may be converted to carbon monoxide gas through the action of the at least one second plasma torch. The second processing chamber may emit 350 the carbon monoxide gas produced therein.

In a parallel processing syngas system configured solely for the production of a syngas, the hydrogen gas and carbon monoxide gas may be combined 355a in a desired ratio to form a syngas mixture. In some examples, the parallel processing syngas system may include a storage facility to store the syngas in one or more containers. Alternatively, the syngas may be placed in one or more containers for shipment to additional facilities for conversion into products.

In another embodiment of a parallel processing syngas system, the system may be configured for the production of a fuel. Such a system may include a process to react 355b the hydrogen gas and carbon monoxide gas in a reaction system to produce the fuel. The type of fuel thus produced may depend on a ratio of the hydrogen gas to the carbon monoxide gas as well as the type of reaction system used to produce the fuel.

As disclosed above, a number of system components may be monitored and/or controlled through one or more controller devices such as a system process controller. In some embodiments, each of the two parallel processing chambers may be controlled by a separate controller. In another embodiment, both processing chambers may be controlled by the same controller. Controllers may have data input from any of a number of sensor devices including, without limitation, temperature sensors, pressure sensors, and gas composition sensors. Controllers may also provide output control signals to any number of actuators and/or valves to control their activities including position of the mechanical components thereof. Controllers may further receive feedback signals from the actuators and/or valves indicating their status or mechanical disposition. One or more heat recovery steam generators may be controlled by means of either a separate controller or by a main or central system controller.

One or more controllers may provide an interface with one or more optional tangible, computer-readable memory devices and a system bus. These memory devices may include, for example, an external or internal DVD or CD ROM drive, a hard drive, flash memory, a USB drive or the like. Additionally, the memory devices may be configured to include individual files for storing any software modules or instructions, auxiliary data, common files for storing groups of results or auxiliary, or one or more databases for storing the result information, auxiliary data, and related information as disclosed above.

Program instructions, software or interactive modules for performing any of the methods and systems as disclosed above may be stored in the ROM and/or the RAM. Optionally, the program instructions may be stored on a tangible computer readable medium such as a compact disk, a digital disk, flash memory, a memory card, a USB drive, an optical disc storage medium, and/or other recording medium.

One or more optional display interfaces may permit information from the bus to be displayed on one or more display devices in audio, visual, graphic or alphanumeric format. The information may include information related to an ongoing fuel production process and associated tasks. Communication with external devices may occur using various communication ports. An exemplary communication port may be attached to a communications network, such as the Internet or an local area network.

The controller hardware may also include an interface that may allow for receipt of data from human communication input devices such as a keyboard or other input devices such as a mouse, a joystick, a touch screen, a remote control, a pointing device, a video input device and/or an audio input device.

In addition to the variety of fuel materials produced by the F-T catalyst, hydrogen gas, directly produced by the primary process chambers, may also be stored as fuel for the use in proton exchange membranes or protonic ceramic fuel cells.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A system comprising:
a first primary processing chamber in operable communication with a source of water through a water inlet, comprising:
at least one first plasma torch,
a first source of a first ionizing working gas for introduction into the at least one first plasma torch,
a first oxygen gas outlet,
a hydrogen gas outlet, and
a water vapor outlet;
a second primary processing chamber in operable communication with a source of carbon dioxide through a carbon dioxide inlet and oxygen through the first oxygen outlet, comprising:
at least one second plasma torch,
a second source of a second ionizing working gas for introduction into the at least one second plasma torch,
a second oxygen gas outlet,
a carbon monoxide gas outlet, and
a carbon dioxide gas outlet; and
a mixing component in fluid communication with the hydrogen gas outlet and the carbon dioxide gas outlet.

2. The system of claim 1, further comprising a reaction system in fluid communication with an outlet of the mixing component.

3. The system of claim 1, further comprising at least one heat recovery steam generator in fluid communication with one or more of the hydrogen gas outlet and the carbon dioxide gas outlet, and configured to produce power.

4. The system of claim 1, further comprising a carbon monoxide gas separator in fluid communication with the carbon monoxide gas outlet.

5. The system of claim 1, further comprising a hydrogen gas separator in fluid communication with the hydrogen gas outlet.

6. The system of claim 1, further comprising an oxygen gas separator in fluid communication with one or more of the first oxygen gas outlet and the second oxygen gas outlet.

7. The system of claim 1, further comprising a controller configured to control the operation of one or more components of the first primary processing chamber, the second primary processing chamber, the mixing component, or any combination thereof.

8. A method of synthesizing syngas comprising:
providing a system for synthesizing syngas comprising:
a first primary processing chamber comprising:
at least one first plasma torch,
a first source of a first ionizing working gas for introduction into the at least one first plasma torch,
a first oxygen outlet,
a hydrogen gas outlet, and
a water vapor outlet,
a second primary processing chamber in operable communication with a source of oxygen through the first oxygen outlet, comprising:
at least one second plasma torch,
a second source of a second ionizing working gas for introduction into the at least one second plasma torch,
a second oxygen outlet,
a carbon monoxide gas outlet, and
a carbon dioxide gas outlet, and
a mixing component in fluid communication with the hydrogen gas outlet and the carbon dioxide gas outlet;
introducing the first ionizing working gas into the at least one first plasma torch, thereby forming at least one first plasma;
introducing water into the first primary processing chamber from a water source;
contacting the water with the at least one first plasma, thereby forming hydrogen gas;
causing the first processing chamber to emit the hydrogen gas from the hydrogen gas outlet;
introducing the second ionizing working gas into the at least one second plasma torch, thereby forming at least one second plasma;
introducing carbon dioxide gas into the second primary processing chamber from a carbon dioxide source;
contacting the carbon dioxide gas with the at least one second plasma, thereby forming carbon monoxide gas;
causing the second processing chamber to emit the carbon monoxide gas from the carbon monoxide gas outlet; and
combining the hydrogen gas and the carbon monoxide gas by the mixing component to produce a syngas.

9. A method of synthesizing a fuel comprising:
providing a system for synthesizing syngas comprising:
a first primary processing chamber comprising:
at least one first plasma torch,
a first source of a first ionizing working gas for introduction into the at least one first plasma torch,
a first oxygen outlet,
a hydrogen gas outlet, and
a water vapor outlet,
a second primary processing chamber in operable communication with a source of oxygen through the first oxygen outlet, comprising:
at least one second plasma torch,
a second source of a second ionizing working gas for introduction into the at least one second plasma torch,
a second oxygen outlet,
a carbon monoxide gas outlet, and
a carbon dioxide gas outlet, and
a mixing component in fluid communication with the hydrogen gas outlet and the carbon dioxide gas outlet;
introducing the first ionizing working gas into the at least one first plasma torch, thereby forming at least one first plasma;
introducing water into the first primary processing chamber from a water source;
contacting the water with the at least one first plasma, thereby forming hydrogen gas;
causing the first processing chamber to emit the hydrogen gas from the hydrogen gas outlet;
introducing the second ionizing working gas into the at least one second plasma torch, thereby forming at least one second plasma;
introducing carbon dioxide gas into the second primary processing chamber from a carbon dioxide source;
contacting the carbon dioxide gas with the at least one second plasma, thereby forming carbon monoxide gas;
causing the second processing chamber to emit the carbon monoxide gas from the carbon monoxide gas outlet; and reacting the hydrogen gas and the carbon monoxide gas in a reaction system thereby producing a fuel.

10. The method of claim 9, wherein the reaction system is a Fischer-Tropsch reaction system.

11. The method of claim 9, wherein the fuel is one or more of diesel fuel, JP-8 fuel, jet fuel, naphtha, and synthetic paraffinic kerosene.

\* \* \* \* \*